(12) United States Patent
Nelson et al.

(10) Patent No.: US 6,242,581 B1
(45) Date of Patent: *Jun. 5, 2001

(54) METHOD FOR PURIFICATION OF RECOMBINANT PROTEINS

(75) Inventors: Paul S. Nelson, Union City; Te-Tuan Yang, Los Altos; Steven R. Kain, Belmont; Thomas H. Smith, San Carlos, all of CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/912,406

(22) Filed: Aug. 18, 1997

Related U.S. Application Data

(63) Continuation-in-part of application No. 08/698,747, filed on Aug. 16, 1996.
(51) Int. Cl.$^7$ ...................................................... C07K 1/22
(52) U.S. Cl. ..................... 530/412; 530/413; 540/200; 540/206; 540/299; 540/320
(58) Field of Search .................................. 530/412, 413; 540/200, 206, 299, 320

(56) References Cited

U.S. PATENT DOCUMENTS 5,047,513 * 9/1991 Dobeli et al. ........................ 530/412

OTHER PUBLICATIONS a) Mantovarra et al. (1991) "Further Characterization of Carboxymethylated Aspartic Acid Agarose. Purification of Human α2–Macroglubulin and Hemopexin" Biotech. & Applied Biochem. 13:371–9.
b) Crowe et al. (1995) "One–Step Purification of Recombinant Proteins with the 6xHis Tag and Ni–NTA Resin" Mol. Biotech. 4:247–58.
Porath et al. 'Immobilized Mettal Inon Affinity Adsoprtion and Immobilizedmetal Affinity Chromatogrpahy of Bioamaterials. Serum Protein Affinities for Gell Immobilized Iron and Nickel Ions', Biochemistry, vol. 22. pp. 1621–1630, 1983.*
Lilius et al. 'Metal Affinity Precipitation of Proteins Carrying Genetically Attached Polyhistidine Affinity Tails', Eur. J. Biochem. vol. 198. pp. 499–504, 1991.*
Mantovaara et al. 'Further Characterization of Carboxymethylated Aspartic Acid Agarose of Human .Alpha. (2)–Macroglobulin and Hemopexin', Biotechnolgy and Applied Biochemistry, vol. 13, pp. 371–379, 1991.*

Mantovaara et al. 'Carboxymethylated Aspartic Acid Agarose, A Selective Adsorbent for Calcium–Binding Proteins, Preliminary Studies', Biotechnolgoy and Applied Biochemistry, vol. 13, pp. 315–322, 1991.*
Porath J. et al. (1975) "Metal chelate affinity chromatography, a new approach to protein fractionation" Nature 258:598–599.
Porath, J. (1992) "Immobilized Metal Ion Affinity Chromatography" Protein Expression and Purification 3:263–281.
Porath, J., B. Olin (1983) "Immobilized Metal Ion Affinity Adsoprtion and Immobilized Metal Ion Affinity Chromatography of Biomaterials. Serum Protein Affinities for Gel–Immobilized Iron and Nickel Ions" Biochemistry 22:1621–1630.
Hochuli, E. et al. (1987) "New Metal Chelate Adsorbent Selective for Proteins and Peptides Containing Neighboring Histidine Residues" Journal of Chromatography 411:177–184.
Ford, C.F. et al. (1991) "Fusion Tails for the Recovery and Purification of Recombinant Proteins" Protein Expression and Purification 2:95–107.
Mantovaara, T. et al. (1989) "Purification of Human Serum Amyloid P Component (SAP) by Calcium Affinity Chromatography" Biotechnology and Applied Biochemistry 11:564–570.
Mantovaara, T. et al. (1991) "Carboxymethylated Aspartic Acid Agarose, a Selective Adsorbent for Calcium–Binding Proteins, Preliminary Studies" Biotechnology and Applied Biochemistry 13:315–322.
Mantovaara, T. et al. (1991) "Purification of Factor VIII:c Coagulant Activity from Rat Liver Nonparenchymalk Cell Culture Medium by Immobilized Metal Ion Affinity Chromatography" Biotechnology and Applied Biochemistry 13:120–126.

* cited by examiner

*Primary Examiner*—Christopher S. F. Low
*Assistant Examiner*—Anish Gupta
(74) *Attorney, Agent, or Firm*—Bozicevic, Field & Francis; Paula A. Borden; Bret E. Field

(57) ABSTRACT

Purification of poly-amino acid-tagged recombinant proteins has been improved by the use of a carboxymethylated aspartate ligand complexed with a third-block transition metal having an oxidation state of $2^+$ and a coordination number of 6. A method for synthesizing the metal ion-CM-Asp complex is also described. Further, the metal ion-CM-Asp complex can be used for screening protein function.

5 Claims, 7 Drawing Sheets

METHOD FOR PURIFICATION OF RECOMBINANT PROTEINS

CROSS-REFERENCE TO A RELATED APPLICATION

This application is a continuation-in-part of co-pending application Ser. No. 08/698,747, filed Aug. 16, 1996.

BACKGROUND OF THE INVENTION

Immobilized metal ion affinity chromatography (IMAC) was first introduced by Porath (Porath, J., J. Carlsson, I. Olsson, G. Belfrage [1975] *Nature* 258:598–599.) under the term metal chelate chromatography and has been previously reviewed in several articles (Porath, J. [1992] *Protein Purification and Expression* 3:263–281; and articles cited therein). The IMAC purification process is based on the employment of a chelating matrix loaded with soft metal ions such as $Cu^{2+}$ and $Ni^{2+}$. Electron-donating groups on the surface of proteins, especially the imidazole side chain of histidine, can bind to the non-coordinated sites of the loaded metal. The interaction between the electron donor group with the metal can be made reversible by lowering the pH or by displacement with imidazole. Thus, a protein possessing electron-donating groups such as histidine can be purified by reversible metal complex/protein interactions.

Several different metal chelating ligands have been employed in IMAC to purify proteins. Iminodiacetic acid (IDA) ligand is a tridentate and thus anchors the metal with only three coordination sites (Porath, J., B. Olin [1983] *Biochemistry* 22:1621–1630). Because of the weak anchoring of the metal, metal leakage has been known to occur. The tris(carboxymethyl)ethylenediamine (TED) ligand is pentadentate and forms a very strong metal-chelator complex. The disadvantage of this is that proteins are bound very weakly since only one valence is left for protein interaction. Nitrilo triacetic acid (NTA) is a tetradentate ligand which attempts to balance the metal anchoring strength with metal-ion protein interaction properties (Hochuli, E., H. Dobeli, A. Schacher [1987] *J. Chromatography* 411:177–184). Other chelating ligands have been reported and are mentioned. See, e.g., Porath (1992), supra. However, these ligands also have certain disadvantages, including decreased bonding capacity, decreased specificity, and increased metal leakage.

In 1991, Ford et al. (Ford, C., I. Suominen, C. Glatz [1991] *Protein Expression and Purification* 2:95–107) described protein purification using IMAC technology (Ni-NTA ligand) as applied to recombinant proteins having tails with histidine residues (polyhistidine recombinant proteins). This method takes advantage of the fact that two or more histidine residues can cooperate to form very strong metal ion complexes. The NTA chelating ligand immobilized on agarose and loaded with $Ni^{2+}$ has been useful in this method (Hochuli et al., supra; U.S. Pat. No. 5,047,513). It is available commercially through Qiagen, Inc. (Chatsworth, Calif.). However, this resin has the disadvantage that the interchanges between metal ions and poly-histidine recombinant proteins are not optimal. Metal leakage can occur, and background proteins can sometimes contaminate purification of recombinant proteins.

A metal chelating gel, i.e., carboxymethylated aspartate (CM-Asp) agarose complexed with calcium, has been used for purifying native calcium-binding proteins (Mantovaara, T., H. Pertoft, J. Porath [1989] *Biotechnology and Applied Biochemistry* 11:564–570; Mantovaara, T., H. Pertoft, J. Porath [1991] *Biotechnology and Applied Biochemistry* 13:315–322; Mantovaara, T., H. Pertoft, J. Porath [1991] *Biotechnology and Applied Biochemistry* 13:120–126). However, the $Ca^{2+}$-CM-Asp complex described by Mantovaara et al., has among its disadvantages that it does not bind strongly to histidine-tagged recombinant proteins. Another disadvantage, in addition to this inferior binding property, is its non-selectivity for histidine tags.

By contrast, the subject invention comprises the CM-Asp chelating ligand complexed to a transition metal in an octahedral geometry (coordination number of 6). In this unique configuration, the metal complex can be advantageously suited for purification of poly-histidine fused recombinant proteins. This is a novel use of the CM-Asp ligand and is part of the subject of the invention herein described.

BRIEF SUMMARY OF THE INVENTION

The present invention concerns a novel IMAC purification method which employs immobilized carboxymethylated aspartate (CM-Asp) ligands specifically designed for purification of recombinant proteins fused with polyhistidine tags. The new purification method is based upon the CM-Asp chelating matrix having the following structure:

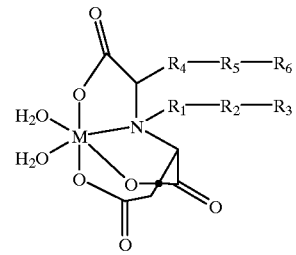

A general description of the matrix used in the invention and illustrated above is:

When $R_4$—$R_5$—$R_6$=H:
M=transition metal ion in a 2+ oxidation state with a coordination number of 6;
$R_1$=a linking arm connecting the nitrogen atom of CM-Asp with $R_2$;
$R_2$=a functional linking group through which CM-Asp linking arm $R_1$ is connected to $R_3$;
$R_3$=a polymer matrix, e.g., those polymer matrices typically used in affinity or gel chromatography.

When $R_1$—$R_2$—$R_3$=H:
$R_4$=a linking arm connecting the methylene carbon atom of the carboxymethyl group of CM-Asp with $R_5$;
$R_5$=a functional linking group through which CM-Asp linking arm R4 is connected to $R_6$;
$R_6$=a polymer matrix, e.g., those polymer matrices typically used in affinity or gel chromatography.

In a preferred embodiment:
M=$Fe^{2+}$, $Co^{2+}$, $Ni^{2+}$, $Cu^{2+}$, or $Zn^{2+}$;
$R_1$=—$CH_2CH(OH)CH_2$—, —$CH_2(OH)CH_2$—O—$CH_2CH(OH)CH_2$—, —$(CH_2)_4NHCH_2CH(OH)CH_2$—, and —$(CH_2)_2NHCH_2CH(OH)CH_2$—;
$R_2$=O, S, or NH; and
$R_3$=agarose.

In a particularly preferred embodiment:
M=$Co^{2+}$;
$R_1$=$CH_2CH(OH)CH_2$;
$R_2$=O; and R₃=agarose, cross-linked.

Prior to loading the 6xHis recombinant protein to the resin, recombinant cells can be lysed and sonicated. The lysate can then be equilibrated with an aqueous buffer (pH 8) which itself does not form chelates with the metal. An example of an aqueous that can be used at this step in the described procedure is 50 mM sodium phosphate (pH 8.0)/10 mM Tris-HCl (pH 8.0)/100 mM NaCl, or the like. The equilibration buffer can contain denaturing agents or detergents, e.g., 10% "TRITON X-100," 6 M guanidinium HCl, or the like. After binding the prepared 6xHis recombinant protein on the metal CM-Asp chelating resin (the "CM-Asp resin complex"), the protein-bound resin is washed at pH 7.0 or 8.0. The elution of the protein can be carried out at a constant pH or with a descending pH gradient. In a preferred embodiment, protein elution can be achieved at a pH of about 6.0 to about 6.3. Alternatively, the 6xHis recombinant protein bound to the CM-Asp chelating resin can be washed with low concentrations (less than 100 mM) of imidazole at pH 8.0 and then eluted by increasing the imidazole concentration to 40–100 mM.

Also included as an aspect of the subject invention is a scaled-up synthesis of the CM-Asp derivatized agarose chelating resin. It is an improved version of a previously reported small scale preparation (Mantovaara, T., H. Pertoft, J. Porath [1991] *Biotechnology and Applied Biochemistry* 13:315–322). The improvement includes particular conditions for oxirane-agarose formation, temperature controlled conjugation of aspartic acid to the oxirane-agarose, and high ionic strength washing to remove extraneously bound metals. These conditions, temperatures, and ionic concentrations are described in detail herein.

An additional application of the subject invention includes screening for protein function on a microtiter plate or filter. The additional applications for the subject invention also include protein-protein interaction studies, as well as antibody and antigen purification. For example, by immobilization of the $Co^{2+}$ moiety onto 96-well plates by CM-Asp, such plates can be used for quantitation of 6xHistidine-tagged protein, protein-protein interaction studies, diagnostic screening for diseases, antibody screening, antagonist and agonist screening for drugs, and reporter gene assays. $Co^{2+}$ can also be immobilized onto a membrane, e.g., a nylon membrane, by CM-Asp, which can be used to lift proteins from expression libraries to make protein libraries from cells. The membranes also can be used for screening of engineered enzymes. Application of the subject invention can also be extended to purification of any interacting molecule, e.g., nucleic acids or small co-factors.

Figure 2A:
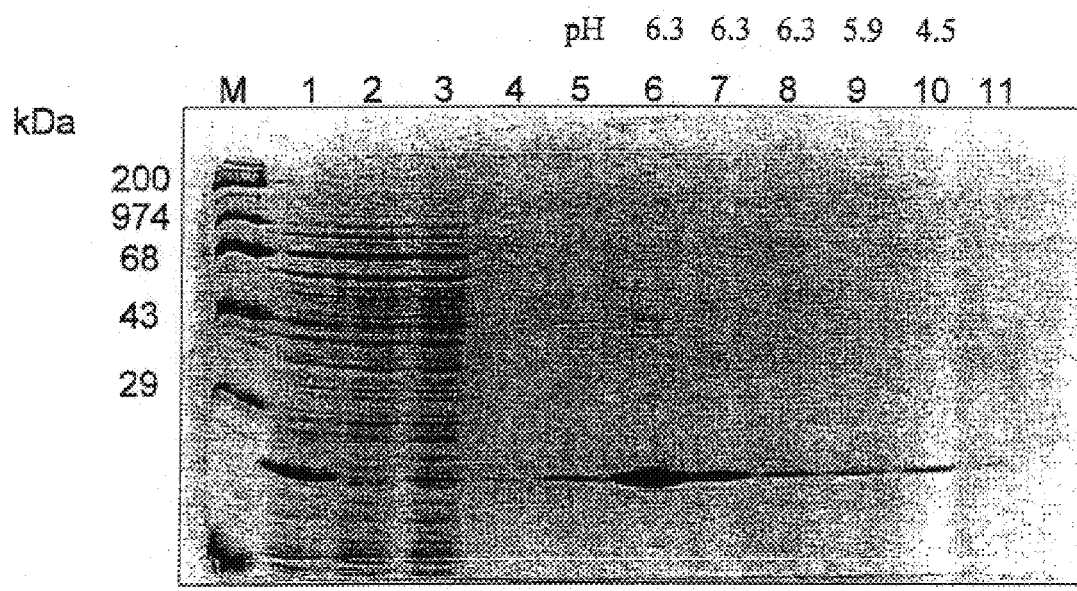
FIGS. 2A–2B show a comparison of $Co^{2+}$ CM-Asp chelating resin with Ni-NTA on 6xHis prepro-α-factor purification under denaturing conditions using pH gradient.
Figure 2B:
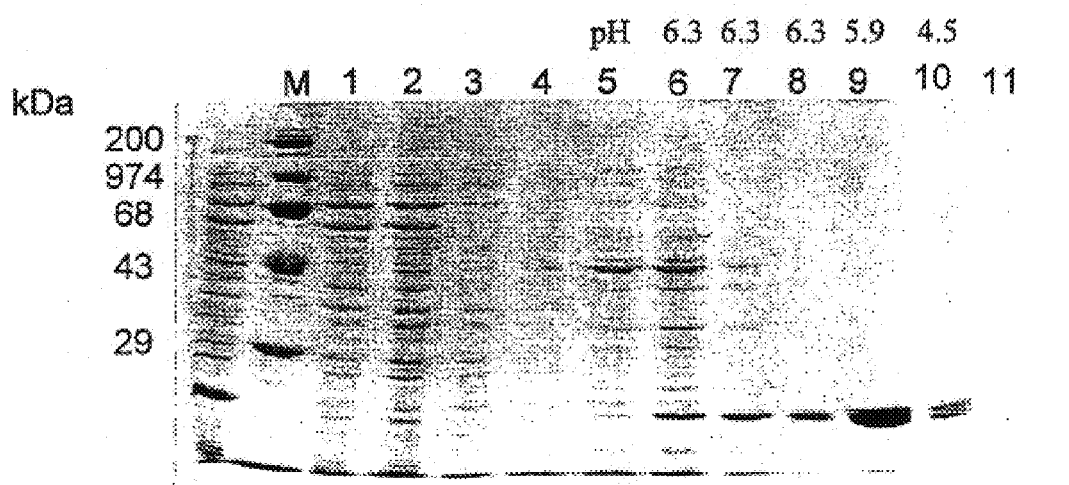

Legend for FIGS. 2A–2B: lane 1: crude lysate; lane 2: flowthrough; lane 3: washed with 6 M Gu-HCl, 0.1 M $NaH_2PO_4$, pH 8.0; lane 4: washed with 8 M urea, 0.1 M $NaH_2PO_4$; lane 5: washed with 8 M urea, 0.1 M $NaH_2PO_4$, pH 8.0; lane 6: deluted with 8 M urea, 0.1 M $NaH_2PO_4$, pH 6.3; lane 7: deluted with 8 M urea, 0.1 M $NaH_2PO_4$, pH 6.3; lane 8: deluted with 8 M urea, 0.1 M $NaH_2PO_4$, pH 6.3; lane 9: deluted with 8 M urea, 0.1 M $NaH_2PO_4$, pH 5.9; lane 10: deluted with 8 M urea, 0.1 M $NaH_2PO_4$, pH 4.5; lane 11: deluted with 6 M Gu-HCl, 0.1 M $NaH_2PO_4$, 0.2 M acetic acid; lane M: MW size markers.

Figure 3:
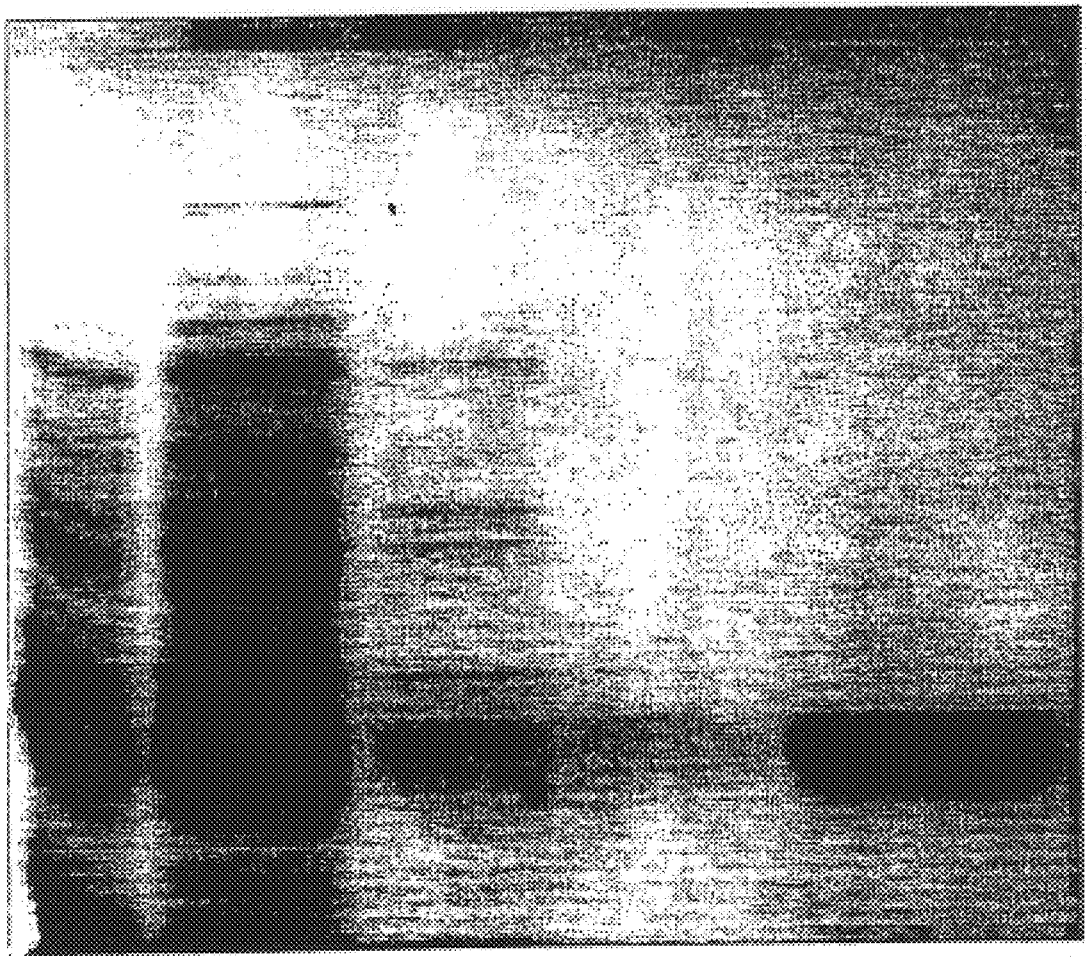

FIG. 3 shows 6xHis tagged DHFR purification by $Co^{2+}$ CM-Asp chelating resin under native conditions. Legend: Lane 1: clarified lysate; lane 2: flowthrough; lane 3: first wash; lane 4: third wash; lane 5: DHFR final elution.

Figure 4:
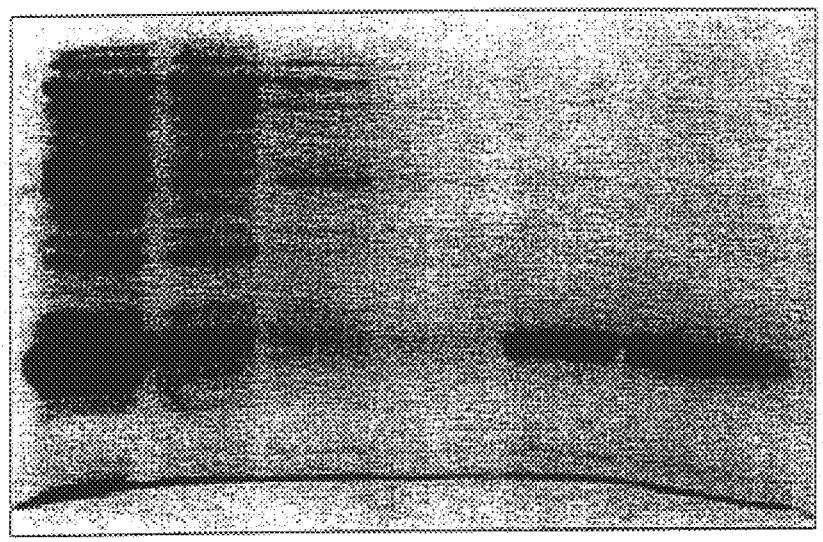

FIG. 4 shows 6xHis tagged DHFR purification by $Co^{2+}$ CM-Asp chelating resin under denaturing conditions. Legend: Lane 1: clarified lysate; lane 2: flowthrough; lane 3: first pH 7.0 wash; lane 4: second pH 7.0 wash; lane 5: DHFR, first pH 6.0 elution; lane 6: DHFR, second pH 6.0 elution.

Figure 5:
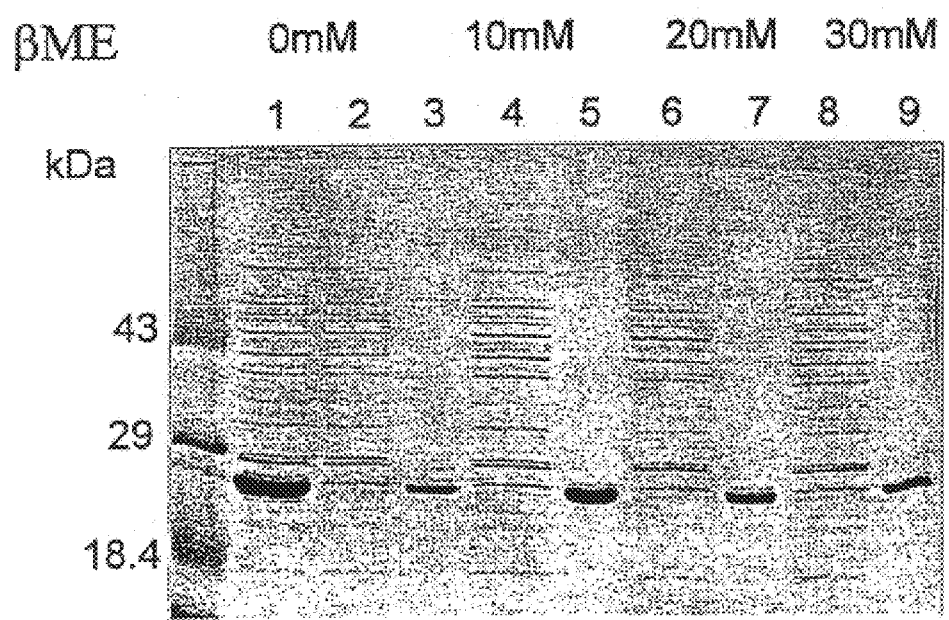

FIG. 5 shows 6xHis tagged DHFR purification by $Co^{2+}$ CM-Asp chelating resin under native conditions with increasing concentrations of β-mercaptoethanol. Legend: lane 1: 20 μl of cell lysate; lanes 2, 4, 6, and 8: 20 μl of flowthrough; lanes 3, 5, 7, and 9: 5 μl of eluant.

Figure 6:
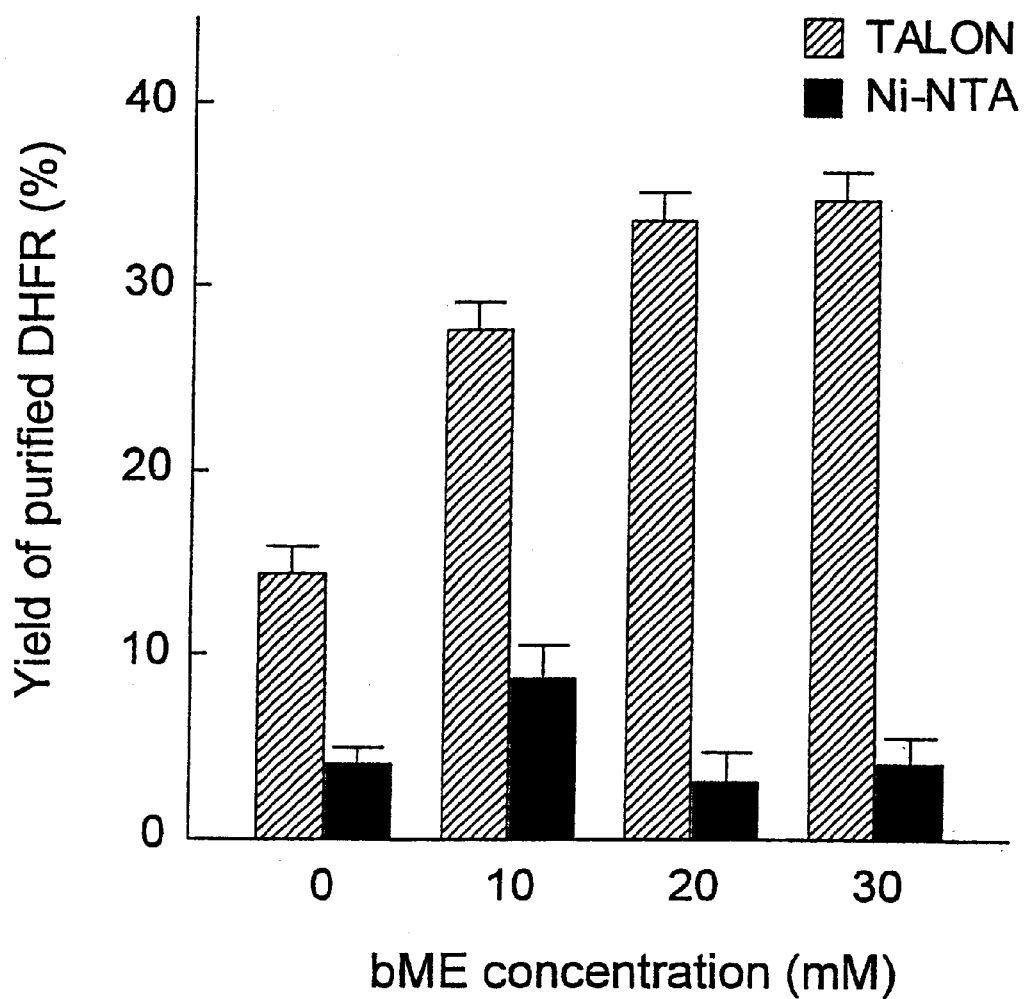

FIG. 6 shows yields of 6xHis DHFR from cell lysates purified by $Co^{2+}$ CM-Asp chelating resin versus Ni-NTA in the presence of β-mercaptoethanol. Protein concentrations were determined by Bradford assay. Yields are expressed as a percentage of total protein in the cell lysate.

Figure 7A:
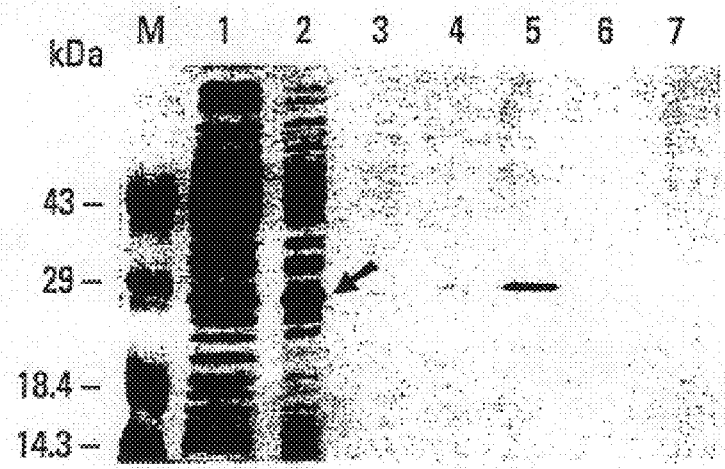
Figure 7B:
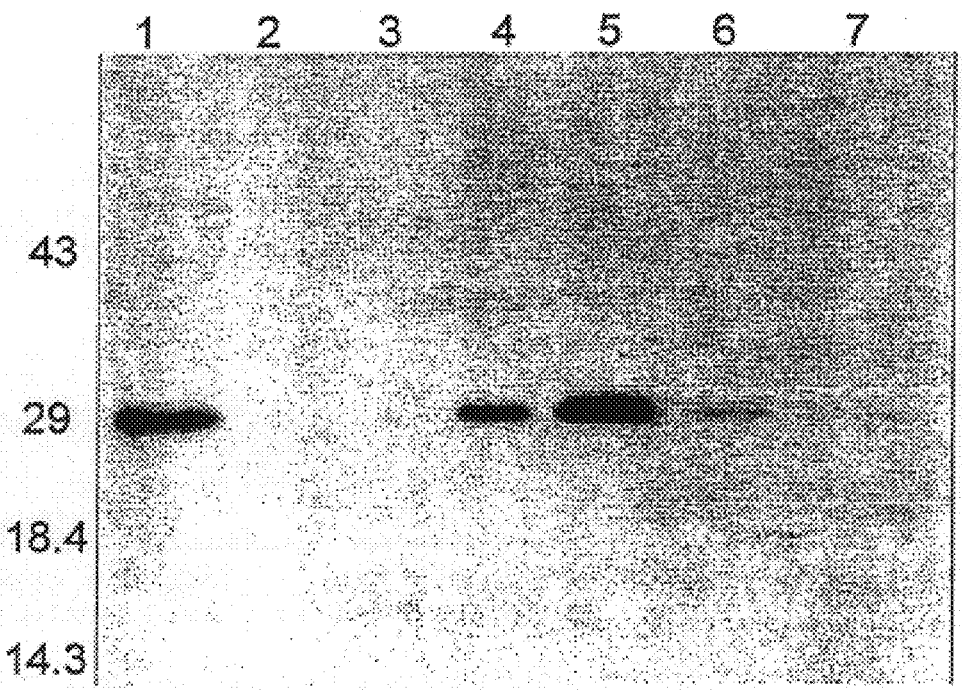

FIGS. 7A–7B show purification of 6xHis GFP by $Co^{2+}$ CM-Asp chelating resin under native conditions. The GFP bands were detected using Clontech's chemiluminescence Western Exposure Kit and overnight exposure to x-ray film.

Legend: lane 1: clarified lysate; lane 2: flowthrough; lane 3: first wash; lane 4: first elution; lane 5: second elution; lane 6: third elution; lane 7: fourth elution.

Figure 8:
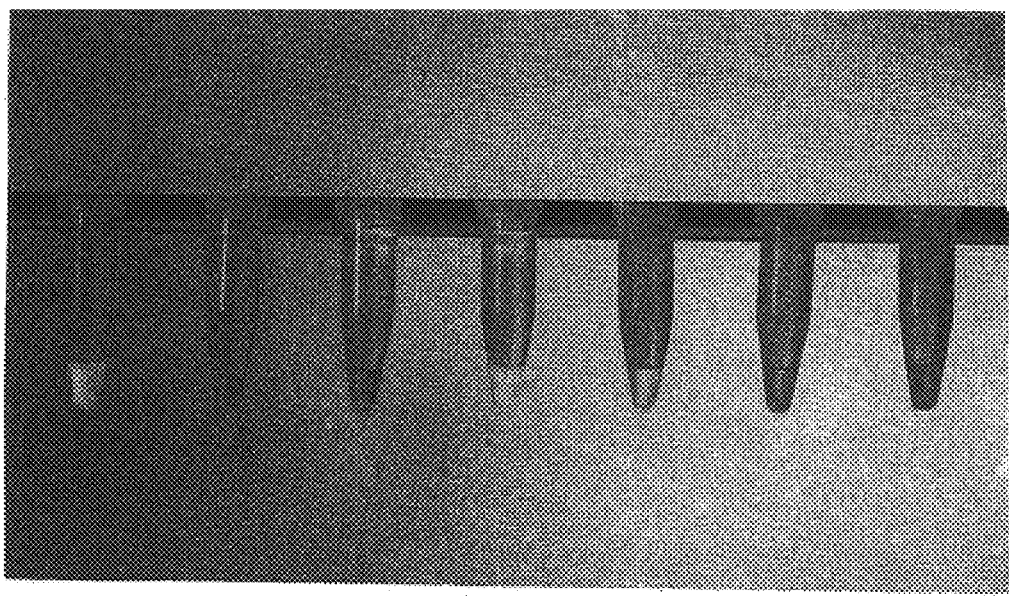

FIG. 8 shows biological activity of 6xHis GFP purified by $Co^{2+}$ CM-Asp chelating resin. Legend: tube 1: cell lysate; tube 3: flowthrough; tube 3: wash; tube 4: first elution; tube 5: second elution; tube 6: third elution.

DETAILED DISCLOSURE OF THE INVENTION

The subject method, which employs a CM-Asp metal chelating complex, can advantageously be used for purification of recombinant proteins having a polyhistidine tail or "tag."

According to one embodiment of the subject invention, a resin ligand, e.g., CM-Asp, is complexed to a metal other than $Ca^{2+}$, forming a CM-Asp-metal complex. Preferably, the CM-Asp ligand used in the subject invention is complexed with one of the transition metals (known as a third-block transition metal), e.g., $Fe^{2+}$, $Co^{2+}$, $Ni^{2+}$, $Cu^{2+}$, or $Zn^{2+}$ in an octahedral geometry. Other polymer matrices, e.g., polystyrene (as in microtiter plates), nylon (as in nylon filters), SEPHAROSE (Pharmacial, Uppeala, Sweden) or the like, can be used with the subject invention and would readily be recognized by persons of ordinary skill in the art. The poly-histidine tag possesses "neighboring" histidine residues which can advantageously allow the recombinant protein to bind to these transition metals in a cooperative manner to form very strong metal ion complexes. This cooperative binding refers to what is commonly known in the art as a "neighboring histidine effect." For purposes of the subject invention, and as would be understood by a person of ordinary skill in the art, a "strong" or "very strong" metal ion complex refers to the bond strength between the metal ion and the chelating ligand. A strong or very strong metal ion complex, for example, allows little or essentially no metal leakage from the complex so that the purified protein, e.g., a recombinant protein having a polyhistidine tag, is not contaminated with undesired or "background" protein from a mixture being purified.

The CM-Asp metal complex offers two available valencies that can form strong and reversible metal complexes with two adjacent histidine residues on the surface of the recombinant protein. Another advantage to using the CM-Asp ligand is its ability to strongly anchor the metal ion whereby metal ion leaking can be virtually eliminated compared to metal leakage observed for other complex binding agents, e.g., Ni-NTA. In a more preferred embodiment, $Co^{2+}$ can be used as the transition metal with CM-Asp. The $Co^{2+}$-CM-Asp can be less sensitive to reducing agents, such as β-mercaptoethanol. Metal ion leakage has been shown to remain low, even negligible, in the presence of up to 30 mM β-mercaptoethanol.

One embodiment of the purification process of the subject invention is as follows:

1. Prepare lysate/sonicate containing recombinant 6×His protein according to standard procedures and techniques well known in the art.
2. Bind 6×His protein onto metal-loaded CM-Asp chelating resin at slightly basic pH, e.g., about pH 8.0.
3. Wash protein/resin complex at the same basic pH (about pH 8.0). Optional washes at a pH of about 7.0 or with imidazole additive can also be included.
4. Elute pure recombinant 6×His protein with an elution buffer having a pH of about 6.0–6.3 or, in the alternative, an elution buffer having a pH of about 8.0, plus about 40 to about 100 mM imidazole.

Figure 1:
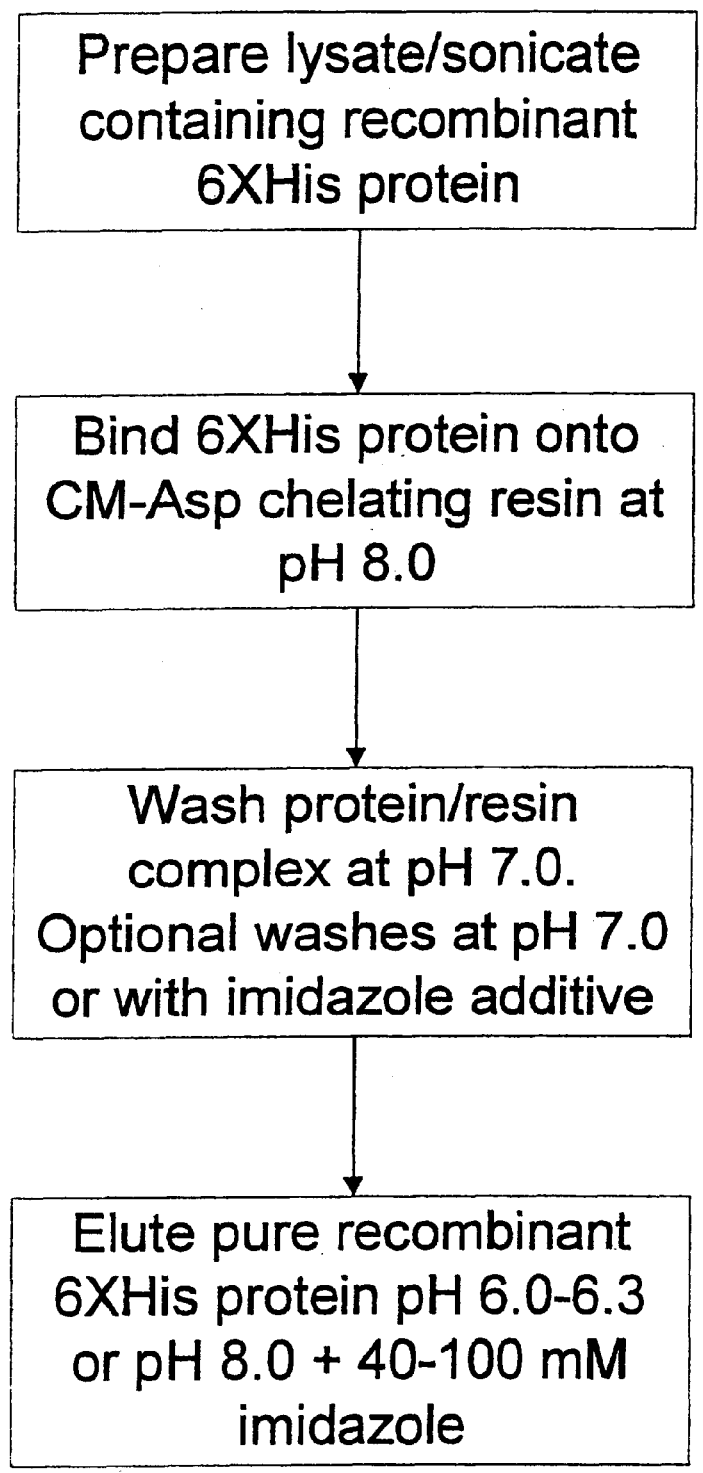
FIG. 1 is an outline illustrating a process for purifying recombinant 6xHis protein using CM-Asp chelating resin.

The steps involved in a preferred embodiment of the purification process of the subject invention are illustrated in FIG. 1. The subject process can be employed batchwise, in spin columns, and in large-scale continuous-flow columns.

Buffers used in the above procedures are standard buffers typically used in similar procedures, with appropriate adjustments and modifications made as understood in the art. For example, a high ionic strength buffer, e.g., 50 mM phosphate/10 mM Tris/100 mM NaCl can be used, with the pH adjusted as needed. The phosphate salt component can range from a concentration of 10–100 mM; Tris from 5–25 mM; and NaCl from 50–200 mM.

Optimal elution conditions depend on the type of impurities, the amount of protein to be purified, and unique properties of the protein, and are determined on a case-by-case basis as would be readily recognized by a person of ordinary skill in the art.

The subject invention also pertains to a method for synthesizing carboxymethylated aspartate chelating matrices, comprising the steps of:

(a) Michael addition of the α-amino function of mono-protected α,ω-diamino acids to maleic acid;
(b) deprotecting the ω-amino functionality; and
(c) attaching the chelator primary amine molecule to a solid matrix.

Following are examples which illustrate procedures for practicing the invention. These examples should not be construed as limiting. All percentages are by weight and all solvent mixture proportions are by volume unless otherwise noted.

EXAMPLE 1
Large-Scale Preparation of CM-Asp Chelating Resin

SEPHAROSE CL-6B or CL-6B (Pharmacia, 8.0 L) is washed with $ddH_2O$, suction dried, and transferred to a 22-L round bottom flask equipped with mechanical stirring. Epichlorohydrin (about 2.0 L) is added, the Sepharose resin mixed to a thick suspension, and allowed to stand at room temperature for about 20 minutes. A solution of sodium hydroxide (about 560 g) and sodium borohydride (about 48 g) in approximately 6400 mL $ddH_2O$ is added and the mixture stirred overnight at ambient temperature. The oxirane-derivatized resin, collected by filtration, is washed ten times with $ddH_2O$ (about 10 L each), once with 10% sodium carbonate (about 10 L), suction dried, and transferred to a 22 L round bottom flask. A specimen of the oxirane derivatized resin treated with 1.3 M sodium thiosulfate is titrated to approximately pH 7.0 to determine the oxirane concentration (preferably, >700 μmol/g).

To a solution of sodium hydroxide (approximately 268 g) in about 7.6 L $ddH_2O$ is added L-aspartic acid (about 575 g) and sodium carbonate (about 1700 g), keeping the temperature below about 25° C. The pH is adjusted to approximately 11.0 and the solution added to the resin. Using mechanical stirring and a heating mantle, the reaction mixture is brought to about 80° C. for 4 hours and allowed to cool to room temperature overnight. The resin was collected by filtration, washed ten times with $ddH_2O$ (about 10 L each), once with 10% sodium carbonate (about 10 L), suction dried, and transferred to a 22-L round bottom flask equipped with mechanical stirring.

To an ice-cooled solution of sodium hydroxide (about 900 g) in 12 L $ddH_2O$ was added bromoacetic acid (about 3000 g) in approximately 750 g increments, keeping temperature below about 30° C. Sodium carbonate (about 660 g) is added and the pH is adjusted to about 10. The resin is reacted with the solution at ambient temperature overnight. The resin is collected by filtration, washed six times with $ddH_2O$ (about 10 L each), six times with 10% acetic acid, and ten times with $ddH_2O$. Washing is continued with $ddH_2O$ until the pH reached about 6.0 by litmus paper. The CM-Asp chelating resin was suction dried in preparation for metal loading.

EXAMPLE 2
Preparation of C-Linked CM-Asp Chelating Resin $N^6$-Carbobenzyloxy-L-lysine (6.15 g) and excess maleic acid (17.6 g) were dissolved in 2 M NaOH (35 mL). The solution was refluxed for 24 hr and allowed to cool to ambient. The pH was adjusted to 3 with 6 M HCl and chilled. The mixture was filtered to remove the unreacted maleic acid which was washed with water (15 mL). The filtrate and washings were combined and evaporated. The residue was dissolved in 4% ammonium formate (120 mL) and degassed briefly. 10% Pd/C (600 mg) was added and the mixture was refluxed under Ar with stirring for 5 hr. The mixture was filtered through celite and the filtrate evaporated. The residue was dissolved in a solution of sodium hydroxide (1.3 g) and sodium carbonate (8.7 g) in dd $H_2O$ (40 mL). The final pH was adjusted to 11. This solution is added to the oxirane-derivatized resin (40 mL bed volume) prepared as described in Example 1. The mixture was stirred at 60° with mechanical stirring for 4 hr and at ambient for 16 hr. The resin was collected by filtration, washed with $ddH_2O$ (6×100 mL), 10% HOAc (6×100 mL), and $ddH_2O$ (6×100 mL) or until the pH reached about 6 by litmus paper test. The C-Linked CM-Asp chelating resin was suction dried in preparation for metal loading.

EXAMPLE 3
Metal Loading of CM-Asp Chelating Resin

The CM-Asp chelating resin of Example 1 (about 1 L of suction dried bed volume) is treated with a transition metal ion solution, e.g., 2 L of either 200 mM of cobalt chloride hexahydrate, nickel sulfate hexahydrate, copper sulfate pentahydrate, or zinc chloride, according to the metal ion deserved. The resin is reacted with the 200 mM metal solution at room temperature for approximately 72 hours and then collected by filtration. The metal loaded CM-Asp chelating resin is washed five times with $ddH_2O$ (about 1 L each), two times with 100 mM NaCl (about 1 L each), six times with ddH$_2$O (about 1 L each), and once with 20% aq. ethanol (about 1 L). The resin can be stored in 20% aq. ethanol.

EXAMPLE 4

Comparison of Co$^{2+}$ CM-Asp Resin with Ni$^{2+}$-NTA on Recombinant 6×His Prepro-α-Factor Under Denaturing Conditions Using pH Gradient For a qualitative comparison of the purification of Co$^{2+}$ CM-Asp chelating resin and Ni-NTA under denaturing conditions, the C-terminal, 6×His-tagged prepro-α-factor of *S. cerevisiae* was expressed in *E. coli*. One gram bacterial cell pellet was lysed in 6 M guanidinium-HCl (Gu-HCl) and 0.1 M NaH$_2$PO$_4$, pH 8.0. Three milliliters of clarified lysate was loaded onto a Co$^{2+}$ CM-Asp chelating resin gravity flow column. The resin-proteins mixture was washed with 8 M urea, 0.1 M NaH$_2$PO$_4$, pH 8.0, and deluted with 8 M urea, 0.1 M NaH$_2$PO$_4$ at three different pHs, 6.3, 5.9, and 4.5. Finally, all bound proteins were deluted with 6 M Gu-HCl, 0.1 M NaH$_2$PO$_4$, 0.2 M acetic acid. Samples from each step were loaded on a 12% polyacrylamide/SDS gel, electrophoresed, and the gel was stained with Coomassie blue. The 6×His-tagged prepro-α-factor was deluted at pH 6.3 as a single prominent band on the gel.

In the same manner, 3 ml of clarified lysate was loaded onto a Ni-NTA gravity flow column. The resin-proteins mixture was washed and deluted the same as above. Samples from each step were loaded on a 12% polyacrylamide/SDS gel, electrophoresed, and the gel was stained with Coomassie blue. There were more than 10 protein bands in elution at pH 6.3. The 6×His-tagged prepro-α-factor was a minor band among them. The majority of the protein was deluted at pH 4.5 without any other contaminant proteins. This demonstrated that the highly purified 6×His-tagged prepro-α-factor was deluted from Co$^{2+}$ CM-Asp chelating resin at the conditions (pH 6.3) under which Ni-NTA was still releasing contaminants. The affinity of Co$^{2+}$ CM-Asp chelating resin to 6×His-tagged prepro-α-factor was more selective than Ni-NTA to the protein.

Results show that highly purified 6×His-tagged protein elutes from Co$^{2+}$ CM-Asp chelating resin while Ni-NTA is still releasing contaminants. See FIGS. 2A–2B: FIG. 2A: Results after using 1 ml of Co$^{2+}$ CM-Asp chelating resin. FIG. 2B: Results after using 1 ml of nickel-NTA.

EXAMPLE 5

Recombinant 6×His DHFR Purification with CM-Asp Resin Under Native Conditions

N-terminal, 6×His-tagged mouse dihydrofolate reductase (DHFR, MW 20.3 kDa) was expressed in *E. coli* cells. Cells were then pretreated with 0.75 mg/ml lysozyme and disrupted in lysis buffer (100 mM NaH$_2$PO$_4$, 10 mM Tris-HCl, pH 8.0) by mechanical shearing, 800 µl of the clarified lysate was applied to 100 µl of Co$^{2+}$ CM-Asp chelating resin, pre-equilibrated with lysis buffer, and washed with one ml of lysis buffer three times. All bound protein was deluted by 300 µl of 100 mM EDTA, pH 8.0. Twenty microliters of lysate and 40 µl of each subsequent fraction from elution were run on a 12% polyacrylamide/SDS gel. The gel was stained with Coomassie blue. One single protein band was shown at a position of MW 20.3 kDa. Results showed the selective binding affinity of Co$^{2+}$ CM-Asp chelating resin to 6×His-tagged DHFR under native purification conditions. No discernable binding of host proteins occurred.

Results show that Co$^{2+}$ CM-Asp chelating resin has selective binding affinity for 6×Histidines. No discernable binding of host proteins occurred. See FIG. 3.

EXAMPLE 6

Recombinant 6×His DHFR Purification with CM-Asp Resin Under Denaturing Conditions N-terminal 6×His-tagged mouse DHFR was expressed in a 25-ml culture of *E. coli*. Cells were pelleted, resuspended in lysis buffer (100 mM NaH$_2$PO$_4$, 10 mM Tris-HCl, 8 M urea, pH 8.0), and disrupted by vortexing. Six hundred microliters of clarified lysate were applied to a Co$^{2+}$ CM-Asp chelating resin spin column containing 0.5 ml of Co$^{2+}$ CM-Asp chelating resin-NX metal affinity resin and centrifuged for 2 minutes at 2,000×g. The column was washed twice with 1 ml of wash buffer (100 mM NaH$_2$PO$_4$, 10 mM PIPES, pH 7.0), and bound proteins were deluted with 600 µl of elution buffer (20 mM PIPES, 100 mM NaCl, 8 M urea, pH 6.0). Twenty microliters of lysate and 40 µl of each subsequent fraction from the elution were loaded onto a 12% polyacrylamide/SDS gel and electrophoresed. The gel was stained with Coomassie blue. One single protein band was shown at the position of 20.3 kDa. Results showed the selective binding affinity of Co$^{2+}$ CM-Asp chelating resin to 6×His-tagged DHFR under denaturing conditions. The binding properties of Co$^{2+}$ CM-Asp chelating resin to 6×histidines allow proteins deluted under mild pH conditions (pH 6.0) that protect protein integrity.

Results show that bound protein can be deluted at mild pH (pH 6.0). This indicates that the binding properties of Co$^{2+}$ CM-Asp chelating resin allow protein elution under mild pH conditions that protect protein integrity. See FIG. 4.

EXAMPLE 7

Recombinant 6×His DHFR Purification with CM-Asp Resin Under Native Conditions with Increasing Concentrations of Beta-Mercaptoethanol N-terminal, 6×His-tagged mouse DHFR was expressed in *E. coli*. Twenty-five milliliters of cell culture were disrupted in 2 ml of sonication buffer (100 mM NaH$_2$PO$_4$, 10 mM Tris-HCl, and 100 mM NaCl, pH 8.0) by freezing and thawing. Then, 2.66 ml of clarified lysate were applied to a 200-µl Co$^{2+}$ CM-Asp chelating resin gravity flow column, pre-equilibrated with the sonication buffer. The proteins/resin mixtures were washed three times with sonication buffer, pH 8.0. All bound proteins were deluted with 600 µl of 100 mM EDTA, pH 8.0. To test the effect of β-mercaptoethanol on the Co$^{2+}$ CM-Asp chelating resin purification under native conditions, all buffers used here contained either 0, 10, 20, or 30 mM β-mercaptoethanol. Samples from each elution were electrophoresed on a 12% polyacrylamide/SDS gel, and the gel was stained with Coomassie blue. One single protein band at the position of MW 20.3 kDa was shown from all elutions. The presence of β-mercaptoethanol did not obsolete the purity of 6×His-tagged DHFR purified by Co$^{2+}$ CM-Asp chelating resin. With up to 30 mM β-mercaptoethanol in all purification buffers, there was no predominant band at 20.3 kDa in flowthroughs, indicating that no loss of metal occurred during protein purification using Co$^{2+}$ CM-Asp chelating resin in the presence of β-mercaptoethanol.

Results show that with up to 30 mM β-mercaptoethanol in the purification buffer, there is no predominant band at 20.3 kDa in the flowthrough, indicating that no loss of metal occurred during protein purification using Co$^{2+}$ CM-Asp chelating resin in the presence of β-mercaptoethanol. See FIG. 5.

EXAMPLE 8

Yields of 6×His DHFR from Cell Lysates Purified by CM-Asp Versus Ni-NTA in the Presence of Beta-Mercaptoethanol N-terminal, 6×His-tagged DHFR was expressed and purified by Co$^{2+}$ CM-Asp chelating resin under native conditions as described in Example 7. Protein concentrations were determined by Bradford assay. Yields were expressed as a percentage of total protein in the cell lysate. The yields of purified 6×His-tagged DHFR were 14%, 28%, 34%, and 35% respectively, with β-mercaptoethanol present in purification buffers at the concentrations of 0, 10, 20, and 30 mM. The protein was purified by Ni-NTA under the same native conditions; the yields of purified 6×His-tagged DHFR were 4%, 8.8%, 3.4%, and 4% respectively with β-mercaptoethanol present in purification buffers at the concentrations of 0, 10, 20, and 30 mM. The yields of purified 6×His-tagged DHFR were significantly higher when using $Co^{2+}$ CM-Asp chelating resin compared to Ni-NTA under native purification conditions with β-mercaptoethanol. This indicates that the metal ion on $Co^{2+}$ CM-Asp chelating resin is strongly anchored to SEPHAROSE beads by a CM-ASP metal chelator that is ideal for binding octahedral metals.

Results show that the yields of purified 6×His DHFR are significantly higher at 10, 20, and 30 mM β-mercaptoethanol using $Co^{2+}$ CM-Asp chelating resin compared to using Ni-NTA. This indicates that the metal ion on $Co^{2+}$ CM-Asp chelating resin is strongly anchored to sepharose beads by CM-Asp metal chelator that is advantageous for binding octahedral metals. See FIG. 6.

EXAMPLE 9

Purification of 6×His GFP by $Co^{2+}$-CM-Asp Under Native Conditions

N-terminal, 6×His-tagged green fluorescent protein (GFP) was expressed in *E. coli* cells. Cells were pelleted, resuspended in sonication buffer (100 mM $NaH_2PO_4$, 10 mM Tris-HCl, and 100 mM NaCl, pH 8.0), and disrupted by freezing and thawing three times. Two milliliters of clarified lysate were applied to 400 μl of $Co^{2+}$ CM-Asp chelating resin, pre-equilibrated with sonication buffer, and washed three times with 2 ml of sonication buffer, pH 8.0. The 6×His-tagged GFP was deluted with 400 μl of 75 mM imidazole buffer containing 20 mM Tris-HCl and 100 mM NaCl, pH 8.0. Samples from each purification step were loaded onto a 12% polyacrylamide/SDS gel, electrophoresed, and the gel was stained with Coomassie blue. One single band was shown at the position of MW 27.8 kDa in the elution with 75 mM imidazole. This demonstrated that 6×His-tagged GFP selectively bound on $Co^{2+}$ CM-Asp chelating resin and can be deluted with low concentration of imidazole under native purification conditions.

Samples from each purification step were also loaded on a 12% polyacrylamide/SDS gel, electrophoresed, and transblotted to a PVDF membrane. The proteins on the blot were probed with anti-GFP monoclonal antibody. One single GFP band was clearly shown in the samples of cell lysate and elution. There was no GFP band shown in flowthrough, which indicated that all expressed GFP in cell lysate was bound to $Co^{2+}$ CM-Asp chelating resin.

Results show that (FIG. 7A) Coomassie blue stained gel shows one single band in 75 mM imidazole elution. This indicates that 6×Histidines selectively bound on $Co^{2+}$ CM-Asp chelating resin. Western analysis data shows no GFP in flowthrough which indicates the high affinity between $Co^{2+}$ CM-Asp chelating resin and 6×histidines (FIG. 7B).

EXAMPLE 10

Biological Activity of 6×His GFP Purified by $Co^{2+}$ CM-Asp

N-terminal, 6×His-tagged GFP was expressed in *E. coli*. Cell lysate was prepared as described in Example 7. The cell lysate was loaded onto a 2-ml $Co^{2+}$ CM-Asp chelating resin Disposable Gravity Column, and purified using the Batch/ Gravity Flow column purification method as described in Example 9. The column was washed with sonication buffer three times and deluted with 100 mM EDTA, pH 8.0. Samples were collected in microfuge tubes from each purification step. The fluorescence of all collected samples was detected using an UltraLum Electronic U.V. Transilluminator. Samples of cell lysate and elution showed strong fluorescence. This experiment demonstrated that 6×His-tagged GFP can be purified to homogeneity by $Co^{2+}$ CM-Asp chelating resin under native conditions and maintains biological activity.

The photo of samples from each purification step shows that GFP can be purified to homogeneity by $Co^{2+}$ CM-Asp chelating resin under native conditions, and the fluorescence indicates that GFP purified by $Co^{2+}$ CM-Asp chelating resin still maintains its biological activity. See FIG. 8.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An immobilized metal ion affinity chromatography purification method for purification of recombinant proteins, said method comprising:

a) providing carboxymethylated aspartate ligand complexed with a transition metal ion in a 2+ oxidation state, having a coordination number of 6;

b) loading a mixture of cell lysate comprising a recombinant protein having a polyhistidine tail to bind with said ligand; and c) eluting said recombinant protein with a suitable elutant to obtain a purified recombinant protein, wherein said transition metal-complexed carboxymethylated aspartate ligand forms a carboxymethylated aspartate chelating matrix which comprises said transition metal and a polymer matrix, wherein said carboxymethylated aspartate chelating matrix has the structure

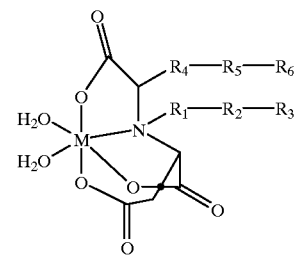

wherein

R1—R2—R3=H;

M=transition metal ion in a 2+ oxidation state with a coordination number of 6;

R4=a linking arm connecting the methylene carbon atom of the carboxymethyl group of Cm-Asp with R5;

R5=a functional linking group through with CM-Asp linking arm R4 is connected to R6; and R6=a polymer matrix.

2. An immobilized metal ion affinity chromatography complex comprising a carboxymethylated aspartate ligand and a transition metal chelated therto, wherein said transition metal ion has a 2+ oxidation state and a coordination number of 6, wherein said complex has the structure:

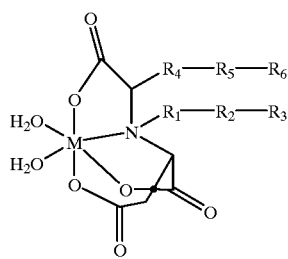

wherein

R1—R2—R3=H;

M=transition metal ion in a 2+ oxidation state with a coordination number of 6;

R4=a linking arm connecting the methylene carbon atom of the carboxymethyl group of Cm-Asp with R5;

R5=a functional linking group through with CM-Asp linking arm R4 is connected to R6; and R6=a polymer matrix.

3. The complex according to claim 2, wherein said polymer matrix comprises a polymer matrix suitable for use in affinity or gel chromatography.

4. The complex according to claim 2, wherein
M=$Fe^{2+}$, $Co^{2+}$, $Ni^{2+}$, $Cu^{2+}$, or $Zn^{2+}$;
$R_4$=—$(CH_2)_4NHCH_2CH(OH)CH_2$— or —$(CH_2)_4NH$—;
$R_5$=O, S, NH, or CO; and
$R_6$=agarose or polystyrene.

5. The complex, according to claim 4, wherein
M=$Co^{2+}$;
R4=—$(CH_2)_4NHCH_2CH(OH)CH_2$— or —$(CH_2)_4NH$—;
R5=O or CO; and
R6=agarose, cross linked agarose, or polystyrene.

* * * * *

UNITED STATES PATENT AND TRADEMARK OFFICE
CERTIFICATE OF CORRECTION

PATENT NO. : 6,242,581 B1
DATED : June 5, 2001
INVENTOR(S) : Paulo S. Nelson et al.

It is certified that error appears in the above-identified patent and that said Letters Patent is hereby corrected as shown below:

Column 10, claim 1,
Lines 54-62, please rewrite as follows:
-- $R_1$-$R_2$-$R_3$=H;
M=transition metal ion in a 2+ oxidation state with a coordination number of 6;
$R_4$=a linking arm connecting the methylene carbon atom of the carboxymethyl group of CM-Asp with $R_5$;
$R_5$=a functional linking group through which CM-Asp linking arm $R_4$ is connected to $R_6$; and
$R_6$=a polymer matrix --.

Column 11, claim 2,
Line 14, please change "R1-R2-R3" to -- $R_1$-$R_2$-$R_3$ --.
Line 17, please change "R4" to -- $R_4$ --.
Line 18, please change "Cm" to -- CM -- and "R5" to -- $R_5$ --.

Column 12, claim 2,
Lines 1 to 3, please rewrite as follows;
-- $R_5$=a functional linking group through which CM-Asp linking arm $R_4$ is connected to $R_6$; and
$R_6$=a polymer matrix --.

UNITED STATES PATENT AND TRADEMARK OFFICE
CERTIFICATE OF CORRECTION

PATENT NO. : 6,242,581 B1
DATED : June 5, 2001
INVENTOR(S) : Paulo S. Nelson et al.

It is certified that error appears in the above-identified patent and that said Letters Patent is hereby corrected as shown below:

Column 12, claim 5,
Line 15, please change "R4" to -- $R_4$ --.
Line 16, please change "R5" to -- $R_5$ --.
Line 17, please change "R6" to -- $R_6$ --.

Signed and Sealed this

Fifteenth Day of January, 2002

*Attest:*

*Attesting Officer*

JAMES E. ROGAN
*Director of the United States Patent and Trademark Office*